(12) United States Patent
Horii et al.

(10) Patent No.: US 7,944,563 B2
(45) Date of Patent: May 17, 2011

(54) SENSING APPARATUS

(75) Inventors: Kazuyoshi Horii, Kanagawa (JP);
Toshihito Kimura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 174 days.

(21) Appl. No.: 12/255,412

(22) Filed: Oct. 21, 2008

(65) Prior Publication Data

US 2009/0103090 A1    Apr. 23, 2009

(30) Foreign Application Priority Data

Oct. 22, 2007 (JP) ................................. 2007-273438

(51) Int. Cl.
*G01N 21/55* (2006.01)
(52) U.S. Cl. ....................................... 356/445
(58) Field of Classification Search ........... 356/445–448
See application file for complete search history.

(56) References Cited

U.S. PATENT DOCUMENTS

| 5,599,668 A | 2/1997 | Stimpson et al. |
| 2005/0186565 A1 * | 8/2005 | Malak .............................. 435/5 |
| 2006/0197952 A1 * | 9/2006 | Chen et al. .................... 356/445 |

FOREIGN PATENT DOCUMENTS

| JP | 8-500667 A | 1/1996 |
| JP | 10-506190 A | 6/1998 |
| WO | 94/00763 A1 | 1/1994 |

\* cited by examiner

*Primary Examiner* — Michael P Stafira
(74) *Attorney, Agent, or Firm* — Sughrue Mion, PLLC

(57) ABSTRACT

The sensing apparatus includes a measuring light emission device, a waveguide member including a sensing surface modified by a surface modification substance, a detection device and an analyzer. The measuring light of a predetermined polarized state is emitted from the emission device so that the measuring light is totally reflected on the sensing surface of the waveguide member holding target substances labeled by fine metal particles to illuminate the particles by evanescent light generated near the sensing surface. The amount of evanescent light scattered by the fine metal particles is detected by the detection device. The measuring light emission device, the waveguide member and the analyzer are included in an optical waveguide system which sets a polarized state of scattered light generated when no target substance is present on the sensing surface in a crossed nicol relation to the analyzer.

10 Claims, 6 Drawing Sheets

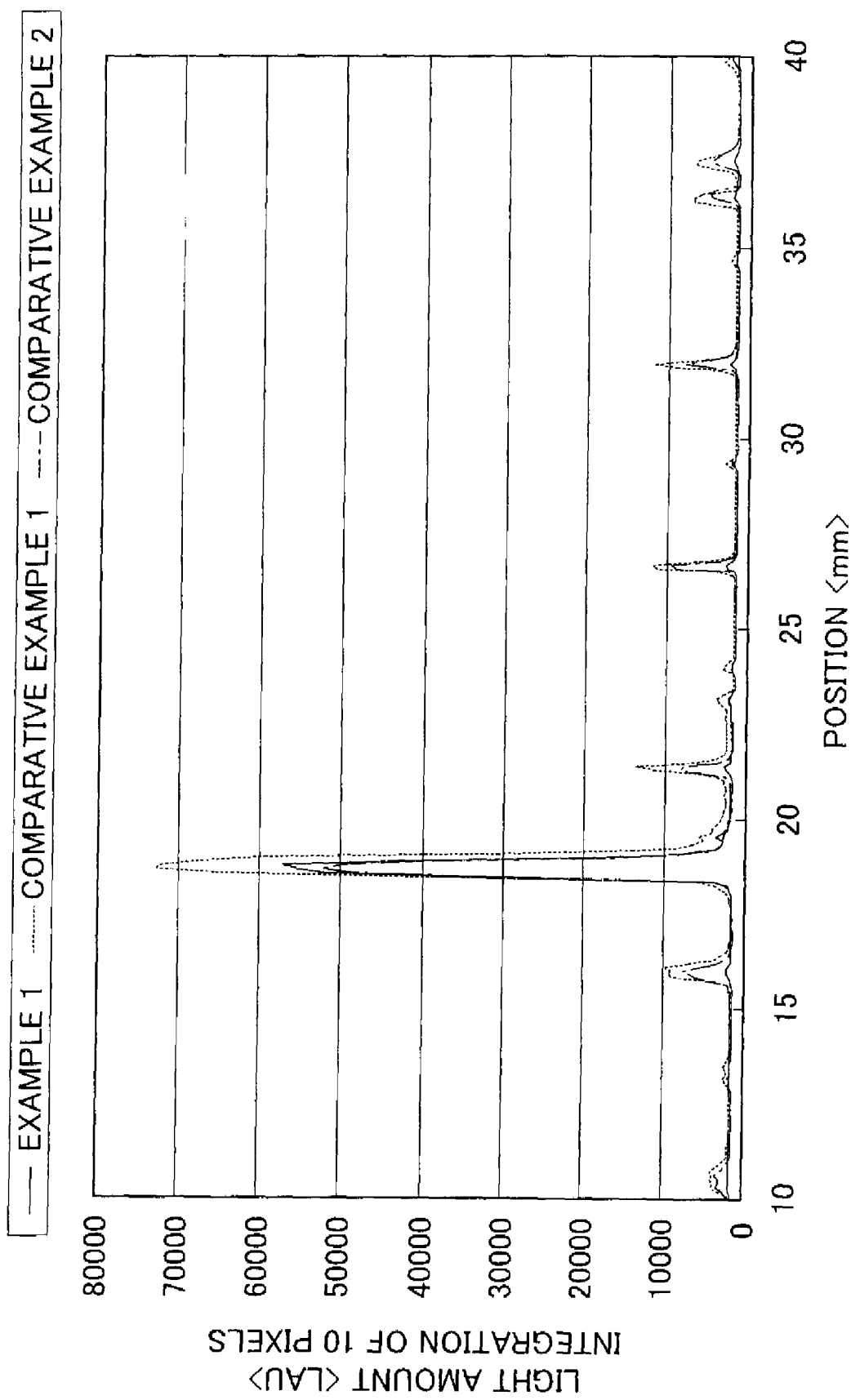

SENSING APPARATUS

The entire contents of literatures cited in this specification are incorporated herein by reference.

BACKGROUND OF THE INVENTION

The present invention relates to a sensing apparatus which detects a target substance by using evanescent light.

When light is incident on a medium of a low refractive index from a medium of a high refractive index, the light is totally reflected at an interface between the two media if its angle of incidence is set equal to or more than a critical angle. In this case, as known, evanescent light is generated to permeate the low refractive-index medium side up to about one wavelength of the light. An area where such evanescent light is generated (evanescent area hereinafter) is a very narrow area of about one wavelength from the interface, i.e., a light reflection surface. Thus, by using the evanescent light, a state of an area in the vicinity of the interface corresponding to the evanescent area can be observed.

Known examples of using evanescent light are a method and an apparatus for detecting presence of a target substance or measuring the amount of a target substance by holding the target substance labeled by a light scattering label of a fine metal particle in an evanescent area, and detecting evanescent light scattered by the light scattering label.

For example, JP 10-506190 A describes a waveguide binding assay method for scattering light by light scattering labels specifically bound to a waveguide element within a penetration depth of an evanescent wave, guiding the scattered light to the waveguide, and detecting a light scattering phenomenon in all areas of the waveguide element by a photodetector such as a CCD camera.

JP 08-500667 A describes a method for binding to binding pair elements an analyte such as an antigen immobilized to other binding pair elements such as antibodies and labeled by a light scattering label in two or more places on a single reactive surface of a cuvette made of an optically transparent material, illuminating the reactive surface with a damped wave (evanescent light wave) generated from an optical beam incident on the transparent material of the reactive surface, and detecting an elastically scattered light obtained from interaction between the damped wave and the light scattering label to detect the immobilized binding pair elements. This Publication further describes separate detection of the binding pair elements in a state being separated in two or more places.

SUMMARY OF THE INVENTION

In the case of the methods described in JP 10-506190 A and JP 08-500667 A, when the light scattered by the light scattering labels is detected, noise light such as scattered light other than the scattered light by the light scattering labels, for example, scattered light generated due to a surface defect such as an irregular surface of the waveguide element or an irregular reactive surface, or scattered light generated due to a foreign object stuck to the surface of the waveguide element or the reactive surface is simultaneously detected, causing a problem of a deteriorated S/N ratio of the detector.

The present invention has been developed to solve the above-mentioned problems of the related art, and it is an object of the present invention to provide a sensing apparatus which can detect evanescent light scattered by a light scattering label with a high S/N ratio, and highly accurately detect a target substance and determine the amount thereof.

In order to achieve the above objects, according to a first aspect of the present invention, there is provided a sensing apparatus, comprising: measuring light emission means for emitting measuring light of a predetermined polarized state; a waveguide member including a sensing surface which is modified by a surface modification substance so that only a specific target substance can be bound thereto, in which the measuring light entering therein under a condition of total internal reflection on the sensing surface is totally reflected to generate evanescent light on the sensing surface; detection means disposed at a side of the waveguide member or outside the waveguide member with respect to the sensing surface to detect an amount of scattered light of the evanescent light; and an analyzer disposed between the waveguide member and the detection means so as to face the sensing surface, wherein: the target substance is labeled by a fine metal particle selectively bound to the target substance; the measuring light emission means, the waveguide member, and the analyzer are included in an optical waveguide system which sets a polarized state of scattered light from the sensing surface generated when the target substance labeled by the fine metal particle is absent on the sensing surface in a crossed nicol relation to the analyzer; and the amount of the evanescent light scattered by the fine metal particle labeling the target substance bound to the surface modification substance modifying the sensing surface is detected by the detection means.

It is preferred that the sensing apparatus further comprise an adjustment mechanism for adjusting a position of the analyzer, wherein the adjustment mechanism adjusts the position of the analyzer so that intensity of the scattered light, which is detected by the detection means via the analyzer, from the sensing surface generated when the target substance labeled by the fine metal particle is absent on the sensing surface is minimum.

Preferably, the measuring light emission means includes a light source for emitting light of an optionally polarized state, and a polarizer for setting the light of the optionally polarized state emitted from the light source as the measuring light of the predetermined polarized state.

It is preferred that the sensing apparatus further comprise an adjustment mechanism for adjusting a position of the polarizer, wherein the adjustment mechanism adjusts the position of the polarizer so that intensity of the scattered light, which is detected by the detection means via the analyzer, from the sensing surface generated when the target substance labeled by the fine metal particle is absent on the sensing surface is minimum.

Preferably, the waveguide member includes a dielectric prism.

Alternatively, It is preferred that the waveguide member include: a plate-shaped waveguide unit for totally reflecting the measuring light at least twice therein; an entrance unit disposed at one end of the plate-shaped waveguide unit to allow the measuring light to enter into plate-shaped waveguide member; and an exit unit disposed at another end of the plate-shaped waveguide unit to allow the measuring light totally reflected at least twice to travel to the outside of the waveguide member.

Preferably, the plate-shaped measuring light emission means emits linearly polarized measuring light as the measuring light of the predetermined polarized state.

Preferably, the measuring light emission means emits one of p-polarized measuring light and s-polarized measuring light as the measuring light of the predetermined polarized state to the sensing surface.

Preferably, the target substance is an antigen; the surface modification substance is a primary antibody bindable to the antigen; the fine metal particle contains secondary antibodies bindable to the antigen on the surface of the fine metal particle; and the evanescent light scattered by the fine metal particle labeling the antigen held on the sensing surface by antigen-antibody reaction is detected by the detection means.

According to the sensing apparatus of the present invention, the optical waveguide system including the measuring light emission means, the waveguide member, and the analyzer sets the polarization state of the scattered light incident on the analyzer in the crossed nicol relation with the analyzer to selectively detect the evanescent light scattered by fine metal particles which are light scattering labels, thereby improving an S/N ratio, and detection of the target substances labeled by the fine metal particles and determination of the amount of the target substances can highly accurately be carried out.

BRIEF DESCRIPTION OF THE DRAWINGS

In the accompanying drawings:

FIG. 5 is a graph illustrating measured values of light amounts in Example 1 and Comparative Examples 1 and 2;

DETAILED DESCRIPTION OF THE PREFERRED EMBODIMENTS

A sensing apparatus of the present invention is described below in detail based on preferred embodiments illustrated in the accompanying drawings.

Figure 1A:
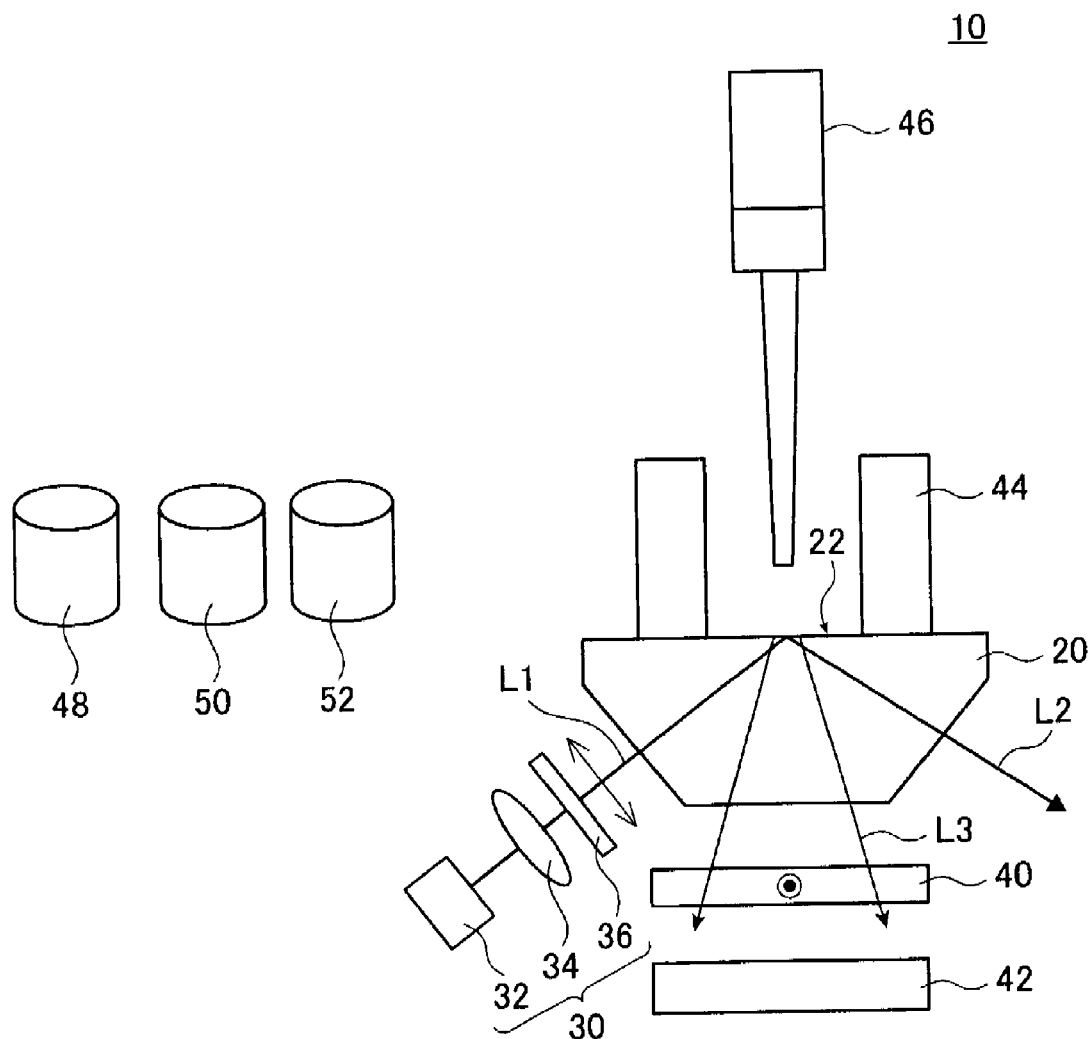
FIGS. 1A and 1B are block diagrams schematically illustrating a sensing apparatus according to a first embodiment of the present invention, FIG. 1A being a front diagram, and FIG. 1B being a top diagram.
Figure 1B:
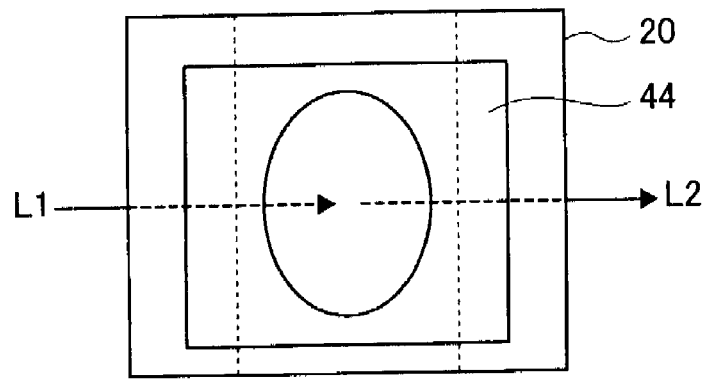
Figure 2:
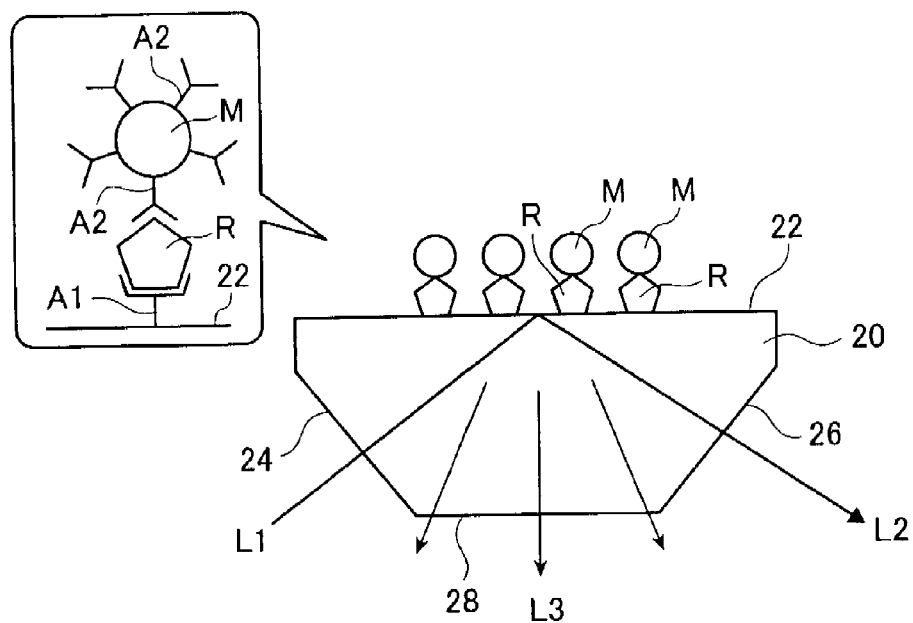
FIG. 2 is a front diagram schematically illustrating a dielectric prism illustrated in FIGS. 1A and 1B.

FIGS. 1A and 1B are block diagrams schematically illustrating a sensing apparatus 10 according to a first embodiment of the present invention, FIG. 1A being a front diagram, and FIG. 1B being a top diagram. FIG. 2 is a sectional diagram illustrating a dielectric prism 20 illustrated in FIGS. 1A and 1B.

The sensing apparatus 10 illustrated in FIGS. 1A and 1B includes an optical waveguide system including the dielectric prism 20, measuring light emission means 30, and an analyzer 40, detection means 42, a reaction vessel 44, a pipet 46, and solution tanks 48, 50, and 52.

Though not illustrated, the sensing apparatus 10 further includes a control unit for controlling an operation of the sensing apparatus 10, and various members necessary for operating the sensing apparatus 10, such as a storage unit for storing various sequences for controlling the operation of the sensing apparatus 10 and detected signals and the like.

The sensing apparatus 10 of the embodiment detects a specific antigen R which is a substance to be detected contained in blood plasma by using antigen-antibody reaction, for example, a sandwich method to determine the amount of the antigen R. More specifically, the sensing apparatus 10 binds together a secondary antibody A2 labeled by a fine metal particle M (surface modification substance A2) and an antigen R, binds the labeled antigen R with a primary antibody immobilized to a surface of the dielectric prism 20 (surface modification substance A1), and detects the antigen R in a state of holding the antigen R labeled by the fine metal particle M on the surface of the dielectric prism 20 to determine the amount thereof.

The sensing apparatus 10 is described below in detail.

The dielectric prism 20 illustrated in FIG. 2 includes, in at least a part of its top surface, a sensing surface 22 having a primary antibody (surface modification substance A1) capable of binding only to a specific antigen (target substance) R.

Measuring light L1 emitted from the measuring light emission means 30 enters the dielectric prism 20 through an entrance surface 24 under a condition of total internal reflection on the sensing surface 22. Light L2 is totally reflected on the sensing surface 22 of the dielectric prism 20 and travels to the outside through an exit surface 26 thereof.

A backside 28 of the dielectric prism 20 is a surface parallel to the sensing surface 22.

In the dielectric prism 20, when the measuring light L1 is totally reflected on the sensing surface 22, evanescent light is generated in the vicinity of the sensing surface 22 outside the dielectric prism 20. This evanescent light illuminates an area of about one wavelength of the measuring light L1 from the sensing surface 22, and the area illuminated with the evanescent light is called an evanescent area.

As illustrated in FIG. 2, by the sandwich method, the antigens R are held on the sensing surface 22 in a state of being beforehand labeled by fine metal particles M having secondary antibodies (surface modification substance A2) selectively bindable to the antigens R. Thus, the fine metal particles M are present in the evanescent area in the vicinity of the sensing surface 22. The fine metal particles M cause scattering of the evanescent light, thereby generating almost randomly polarized scattered light L3. The scattered light L3 is light scattered by the fine metal particles M to travel to the inside of the dielectric prism 20.

The fine metal particle M should have sufficient sizes and shapes to enable scattering of the evanescent light. Sizes of fine metal particles only need to be within a range in which antigen-antibody reaction is not inhibited, generally 10 nm to 1 μm. There is no limitation on materials. In view of using fine metal particles as light scattering labels in the antigen-antibody reaction, however, materials highly stable chemically such as Au, Pt, Ag, and Cu are preferable.

The measuring light emission means 30 emits measuring light L1 in a predetermined polarized state, and includes a light source 32, a condenser lens 34, and a polarizer 36. Light emitted from the light source 32 is condensed by the condenser lens 34 to be a condensed beam, and then changed for its polarized state by the polarizer 36 to be linearly polarized measuring light L1. According to this embodiment, an emission direction of the measuring light L1 emitted from the measuring light emission means 30 and a position of the polarizer 36 are set so that p-polarized measuring light L1 impinges on the sensing surface 22.

The measuring light emission means 30 may include various optical members such as a collimator lens and a polarizing plate as occasion demands.

The analyzer 40 is disposed between the dielectric prism 20 and the detection means 42 so as to face the sensing surface 22. According to the embodiment, the analyzer 40 is disposed in a crossed nicol relation to a polarizing direction of the measuring light L1 incident on the sensing surface 22. In other words, the analyzer 40 is disposed so as to transmit only s-polarized light with respect to the sensing surface 22.

The detection means 42 is disposed inside the dielectric prism 20 with respect to the sensing surface 22. In other words, the detection means 42 is disposed on a bottom surface 28 side to detect the amount (intensity) of evanescent light scattered by a fine metal particle M labeling a target substance R via the analyzer 40. For the detection means 42, various photodiodes capable of detecting the amount (intensity) of the scattered light can be used.

The reaction vessel 44 is a casing disposed to surround the sensing surface 22 of the dielectric prism 20. The reaction vessel 44 receives various solutions stored in the solution tanks 48, 50, and 52. The sensing apparatus 10 of this embodiment carries out antigen-antibody reaction of the antigen R in the reaction vessel 44 to immobilize the antigen R labeled by the fine metal particle M on the sensing surface 22.

The pipet 46 sucks and dispenses a predetermined amount of a solution stored in one of the solution tanks 48, 50, and 52 or the reaction vessel 44. The pipet 46 repeats solution sucking and discharging, and stirs the solution stored in one of the solution tanks 48, 50, and 52 or the reaction vessel 44. Dispensation and stirring of various solutions by the pipet 46 may automatically be carried out by a drive mechanism (not shown) of the pipet 46, or manually by a user.

The solution tanks 48, 50, and 52 store different solutions. According to the embodiment, the solution tank 48 stores blood plasma containing the antigen R. The solution tank 50 stores fine metal particles M whose surfaces are modified by secondary antibodies A2, i.e., the secondary antibodies A2 labeled by the fine metal particles M. The solution tank 52 stores phosphate buffered saline (PBS).

The secondary antibody A2 labeled by the fine metal particle M is also referred to as a labeled secondary antibody hereinafter.

The sensing apparatus 10 thus configured allows p-polarized measuring light L1 to be incident on the sensing surface 22, and totally reflects the measuring light L1 to generate evanescent light in the evanescent area in the vicinity of the sensing surface 22 outside the dielectric prism 20. This evanescent light is scattered by the fine metal particles M labeling the antigens R held on the sensing surface 22 by antigen-antibody reaction to generate scattered light L3. The scattered light L3 is transmitted through the dielectric prism 20 to travel to the outside through the bottom surface 28. The light L3 scattered to the outside through the bottom surface 28 of the dielectric prism 20 is detected by the detection means 42 via the analyzer 40.

The light L3 scattered by the fine metal particles M is almost randomly polarized light. It is because the evanescent light is radiated after being absorbed by the fine metal particles M, thereby changing a polarization state.

On the other hand, noise light such as scattered light generated by scattering of the measuring light L1 or the evanescent light due to defects such as irregular patterns of the sensing surface 22, or scattered light generated by scattering of the evanescent light caused by foreign objects other than the fine metal particles M stuck to the sensing surface 22 holds a polarization state (polarized state) of the measuring light L1. In other words, according to the embodiment, a p-polarized state is maintained with respect to the sensing surface 22.

The sensing apparatus 10 of the embodiment detects the scattered light via the analyzer 40 disposed in the crossed nicol relation to the polarizing direction of the measuring light L1. Thus, components other than the s-polarized component of the light having transmitted through the analyzer 40 are eliminated. In other words, p-polarized noise light is eliminated, and only the s-polarized component of the scattered light L3 is detected by the detection means 42.

In the sensing apparatus 10, the noise light is eliminated by the analyzer 40 to enable selective detection of only the scattered light L3 of the evanescent light scattered by the fine metal particles M. Thus, an S/N ratio can be increased, and highly accurate measurement can be carried out.

Further, the noise light caused by the surface irregularities and the like of the sensing surface 22 of the dielectric prism 20 can be eliminated. Thus, even when an inexpensive dielectric prism 20 low in forming accuracy is used, an S/N ratio can be increased, and highly accurate measurement can be carried out.

An example of a detection method of an antigen R, which uses the sensing apparatus 10 of this embodiment, is described. The solutions stored in the solution tanks 48, 50 and 52 and the reaction vessel 44 are moved and stirred by the pipet 46.

First, 50 μl of PBS is dispensed in the reaction vessel 44 covering the sensing surface 22 to which primary antibodies A1 have been attached.

The light source 32 is turned on to record a signal P0 detected by the detection means 42. The signal P0 is a signal indicating a light amount detected by the detection means 42 when no fine metal particles M are present in the evanescent area on the sensing surface 22 (when no scattered light L3 is generated).

The signal P0 is a signal indicating the amount of noise light caused by stray light or scattered light that could not be completely eliminated by the analyzer 40 even in the sensing apparatus 10 of the embodiment. After the recording of the signal P0, the light source 32 is turned off.

Then, 40 μl of PBS is discharged from the reaction vessel 44.

Then, 50 μl of blood plasma is dispensed from the solution tank 48 storing the blood plasma into the solution tank 50 storing the labeled secondary antibodies, and stirred several times. Thus, the labeled secondary antibodies are bound to specific antigens R in the blood plasma, and the antigens R are labeled by fine metal particles M.

Then, 40 μl of a solution including the antigens R labeled by the fine metal particles M is dispensed from the solution tank 50 into the reaction vessel 44, and the solution of the reaction vessel 44 is repeatedly stirred. Thus, the antigens R labeled by the fine metal particles M and the primary antibodies A1 immobilized on the sensing surface 22 are bound together. In other words, the antigens R which are bound to the labeled secondary antibodies to be labeled by the fine metal particles M are immobilized on the sensing surface 22.

The reaction vessel 44 is cleansed a plurality of times. Specifically, a series of steps of discharging 40 μl of the solution from the reaction vessel 44, then dispensing 40 μl of PBS into the reaction vessel 44, and stirring a plurality of times are set as one cleansing operation, and this operation is repeated a plurality of times, for example, four times. Thus, an antigen R not bound to the primary antibody A1, a labeled secondary antibody not bound to the antigen R, or foreign objects such as various proteins contained in the blood plasma other than the antigen R are eliminated from the reaction vessel 44.

Then, the light source 32 is turned on to record a signal P1 detected by the detection means 42. The signal P1 is a signal indicating the amount of light including the noise light detected as the signal P0 in addition to the scattered light L3 of the evanescent light by the fine metal particles M labeling the antigens R. After the recording of the signal P1, the light source 32 is turned off.

By taking a difference between the signals P0 and P1 thus detected, the amount (intensity) of the scattered light L3 can be obtained. In this case, by establishing beforehand a relation between the amount of the scattered light L3 and the number of fine metal particles M (number of labels) to create a table indicating a correlation between the amount of the scattered light L3 and the number of labels, the number of labels corresponding to the amount of the scattered light L3 obtained as the difference value between the signals P0 and P1 can be specified. The number of antigens R bound to the primary antibodies A1 on the sensing surface 22 corresponds to the number of labels. Thus, by specifying the number of labels, the number of antigens R bound to the primary antibodies, in other words, the amount of binding, can be specified, and quantitatively measured.

In the sensing apparatus 10 of the embodiment, the polarizer and the analyzer may include adjustment mechanisms for adjusting angles and positions so that they can adjust their angles and positions. Angles and positions of the polarizer 36 and/or the analyzer 40 may be manually or automatically adjusted so that, for example, a value of the signal P0 can be minimum.

Thus, in the optical waveguide system including the dielectric prism 20, the measuring light emission means 30, and the analyzer 40, the angles and the positions of the polarizer 36 and/or the analyzer 40 are adjusted so that the value of the signal P0 can be minimum even when a polarized state of light incident on the analyzer 40 is deviated from the crossed nicol relation with respect to the analyzer 40, whereby the noise light can be more surely eliminated.

According to the embodiment, by adjusting the direction in which the measuring light L1 is emitted from the measuring light emission means 30 and the orientation of the polarizer 36, the p-polarized light is allowed to be incident on the sensing surface 22. However, this arrangement is in no way limitative of the present invention. The s-polarized light may be allowed to be incident on the sensing surface 22. In this case, the analyzer 40 is disposed so as to transmit only the p-polarized light therethrough with respect to the sensing surface 22.

The present invention is not limited to the entrance of the p-polarized or s-polarized light on the sensing surface. A linearly polarized measuring light having a polarized surface inclined with respect to the sensing surface may impinge thereon. In this case, elliptically polarized light is generated as noise light. Thus, a wavelength plate for converting a polarized state of this elliptically polarized noise light into a linearly polarized state only needs to be disposed on an upstream side of the analyzer to constitute an optical waveguide system. According to the embodiment, for example, a wavelength plate may be disposed between the dielectric prism 20 and the analyzer 40, and the analyzer 40 only needs to be disposed in a crossed nicol relation to the light transmitted through the wavelength plate to be converted into the linearly polarized light.

The sensing apparatus 10 includes the pipet 46 and the solution tanks 48, 50, and 52. However, the present invention is not limited to this arrangement. The pipet 46 and the solution tanks 48, 50, and 52 may be prepared separately from the sensing apparatus, and prepared when necessary.

In the sensing apparatus 10, the measuring light emission means 30 is not limited to the aforementioned configuration. The measuring light emission means 30 may include a light source for emitting light in an optionally polarized state (e.g., randomly polarized light), and a polarizer for setting the light in an optionally polarized state as measuring light in a predetermined polarized state.

According to the embodiment, the sandwich method is used for holding the antigen R on the sensing surface. However, the present invention is not limited to this method. A competitive method may be used. When the competitive method is used, for example, a sample including antigens R labeled and not labeled by fine metal particles M is beforehand brought into contact with the sensing surface having the primary antibodies, and the antigens R are captured by the primary antibodies through antigen-antibody reaction to hold the antigens R labeled by the fine metal particles M on the sensing surface.

This embodiment has been described on the sensing apparatus which holds the antigen R labeled by the labeled secondary antibody on the sensing surface by using the primary antibody (surface modification substance A1) and the secondary antibody (surface modification substance A2) specifically binding to the antigen (target substance R) through antigen-antibody reaction, and detects the antigen held on the sensing surface and determines the amount thereof. However, the present invention is not limited to this embodiment.

In the sensing apparatus of the present invention, any surface modification substance A1 may be used on the sensing surface as long as it specifically binds to the target substance R. For its binding method, chemical binding or physical adsorption may be used.

The surface modification substance A2 on the surface of the fine metal particle M which is a light scattering label is not particularly limited as long as it can bind to the target substance R. For its binding method, chemical binding or physical adsorption may be used.

A second embodiment of a sensing apparatus of the present invention is described below.

Figure 3:
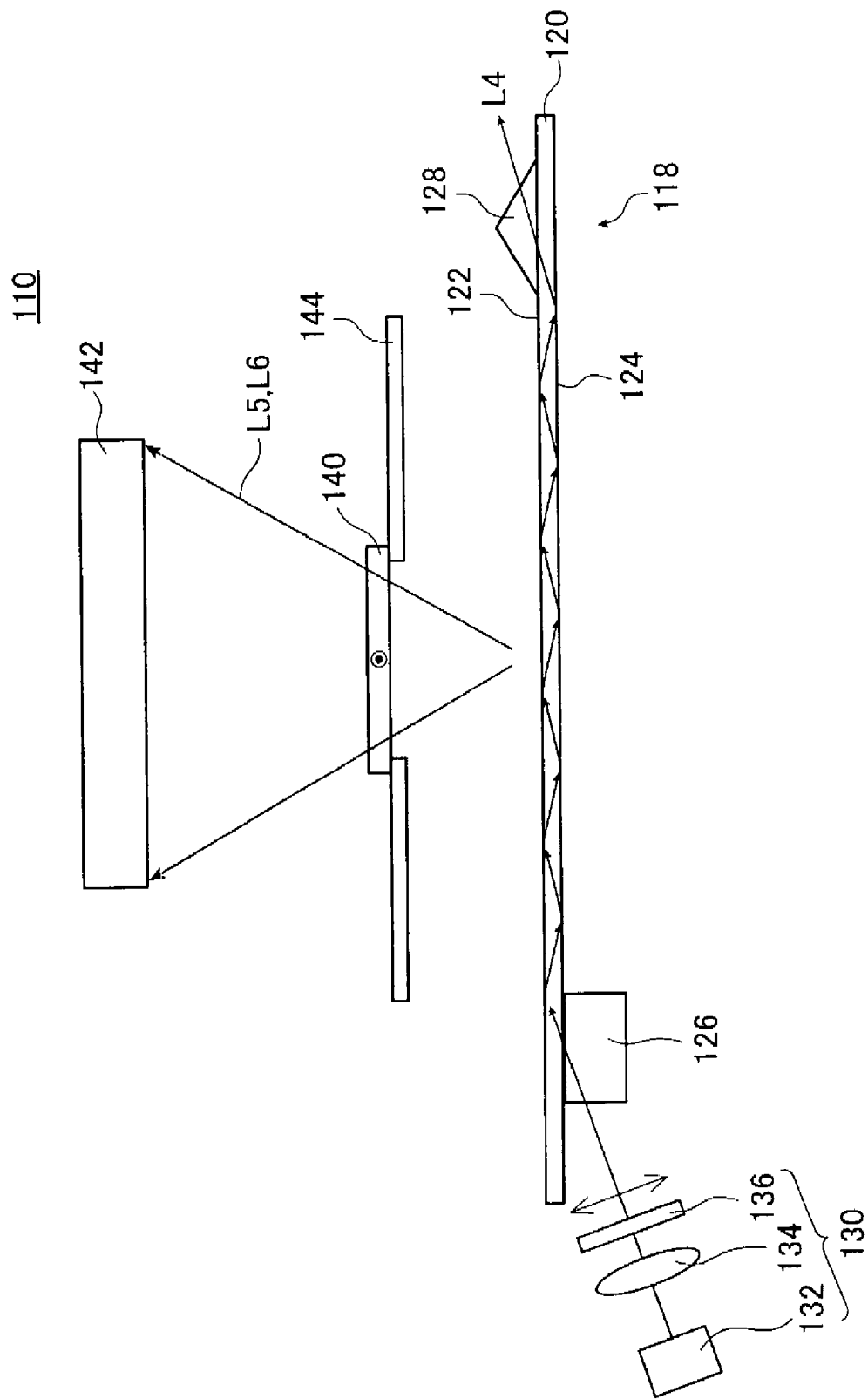
FIG. 3 is a front diagram schematically illustrating a configuration of a sensing apparatus according to a second embodiment of the present invention.

FIG. 3 is a front diagram schematically illustrating a configuration of a sensing apparatus 110 of the second embodiment.

The sensing apparatus 110 illustrated in FIG. 3 includes a waveguide member 118 including a slide glass 120 and entrance and exit prisms 126 and 128, measuring light emission means 130, an analyzer 140, detection means 142, and an aperture 144.

As in the case of the sensing apparatus 10 illustrated in FIGS. 1A and 1B, the sensing apparatus 110 of the embodiment detects a specific antigen R contained in blood plasma to determine the amount thereof. In the sensing apparatus 110, an antigen R labeled by a labeled secondary antibody is bound to a primary antibody immobilized on a surface of the slide glass 120, and the antigen is detected in a state of holding the antigen to determine the amount thereof.

The measuring light emission means 130 is basically similar to the measuring light emission means 30 illustrated in FIG. 1A, and emits measuring light L4 of a linearly polarized state. According to this embodiment, the measuring light emission means 130 sets an emission direction of an optical beam from a light source 132 and a direction of a polarizer 136 so that p-polarized measuring light L4 can be incident on a sensing surface 122 of the slide glass 120 described below. For the light source 132, for example, an SHG laser light source for emitting light of a wavelength 532 nm can be used.

The waveguide member 118 includes the slide glass 120 (waveguide unit), the entrance prism 126 (light entrance unit) disposed at one end of the slide glass 120, and the exit prism 128 (exit unit) disposed at the other end of the slide glass 120.

The waveguide member 118 allows the measuring light L4 from the measuring light emission means 130 to enter therein from one end of the slide glass 120 through the entrance prism 126. The waveguide member 118 totally reflects the entered measuring light L4 a plurality of times in the slide glass 120 to guide it to the other end of the slide glass 120. The measuring light L4 that has reached the other end of the slide glass 120 travels to the outside of the waveguide member 118 through the exit prism 128. Thus, the measuring light L4 can be prevented from being reflected on the other end side of the slide glass 120 to return to the entrance side.

The slide glass 120 is a plate-shaped member including the sensing surface 122 and a backside 124 parallel to the sensing surface 122, and totally reflects the measuring light L4 a plurality of times between the sensing surface 122 and the backside 124 to guide it from one end thereof to the other end.

A primary antibody A1 to which only a specific antigen R can be bound is attached to the sensing surface 122, whereby the sensing surface 122 can hold the antigen R. According to this embodiment, for example, by a sandwich method, the antigen R labeled by a labeled secondary antibody is beforehand bound to a primary antibody to set a state where the antigen R labeled by a fine metal particle M is held on the sensing surface 122.

When the measuring light L4 entering into the slide glass 120 under a condition of total internal reflection on the sensing surface 122 is totally reflected on the sensing surface 122, evanescent light is generated in the vicinity (evanescent area) of the sensing surface 122 outside the slide glass 120. According to this embodiment, the measuring light L4 is totally reflected on the sensing surface 122 a plurality of times, and evanescent light is generated in each total internal reflection position of the measuring light L4 to form an evanescent area.

Figure 4A:
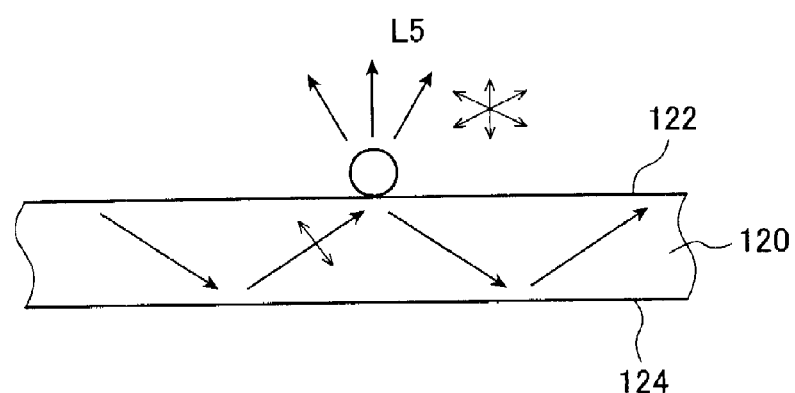
FIGS. 4A and 4B are diagrams illustrating a situation where scattered light is generated at a sensing surface of a slide glass illustrated in FIG. 3.

FIG. 4A illustrates a case where a fine metal particle M is present in the evanescent area. FIG. 4A illustrates only the fine metal particle M. In reality, however, an antigen R labeled by fine metal particle M is held on the sensing surface 122 by a primary antibody. When the fine metal particle M are present in the evanescent area, evanescent light is scattered by the fine metal particle M to generate a randomly polarized scattered light L5 which travels to the outside of the slide glass 122.

Figure 4B:
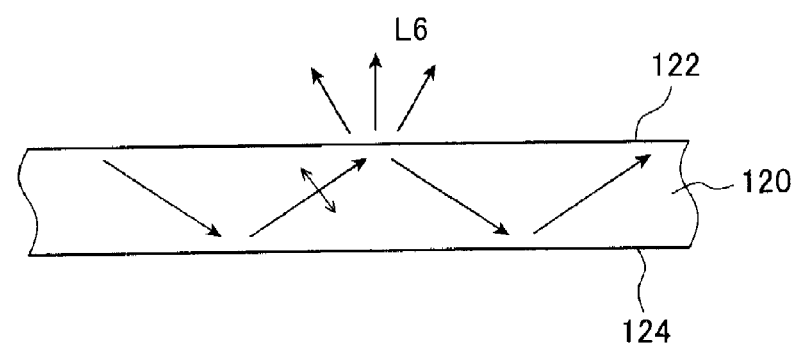

FIG. 4B illustrates a case where no fine metal particle M is present in the evanescent area. As illustrated in FIG. 4B, when no fine metal particle M is present in the evanescent area, only noise light L6 such as scattered light generated by scattering of the measuring light L4 or the evanescent light due to defects such as irregularities of the sensing surface 122, or scattered light generated by scattering of the evanescent light due to foreign objects other than fine metal particles M stuck to a surface of the sensing surface 122 is generated. This noise light L6 holds a polarized state of the measuring light L4. In other words, a p-polarized state is maintained with respect to the sensing surface 122.

The aperture 144 is disposed so as to face the sensing surface 122, and includes an opening for transmitting only the scattered light L5 and the noise light L6 generated in predetermined areas of the sensing surface 122. By the aperture 144, scattered light or stray light other than the scattered light L5 and the noise light L6 generated in the predetermined areas of the sensing surface 122 can be eliminated.

The analyzer 140 is disposed between the aperture 144 and the detection means 142 so as to be integral with the aperture 144, and so as to face the sensing surface 122. The analyzer 140 is disposed in a crossed nicol relation to a polarizing direction of the measuring light L4 incident on the sensing surface 122. In other words, the analyzer 140 is disposed so as to transmit only s-polarized light with respect to the sensing surface 122.

The detection means 142 is disposed outside a dielectric prism with respect to the sensing surface 122, and detects via the analyzer 140 the amount (intensity) of evanescent light scattered by fine metal particles M labeling target substances R. For the detection means 142, various imaging devices such as a CCD capable of detecting the amount (intensity) of the scattered light, or various photodiodes can be used.

According to this embodiment, the aperture 144, the analyzer 140, and the detection means 142 can be integrally moved by a moving mechanism (not shown) in a direction parallel to the sensing surface 122, and the sensing surface 122 is scanned from an end of an entrance side of the measuring light L4 to an end of an exit side.

The sensing apparatus 110 thus configured totally reflects the measuring light L4 on the sensing surface 122 a plurality of times to generate evanescent light in the evanescent area in the vicinity of the sensing surface 122. This evanescent light is scattered by the fine metal particle M of the target substance R labeled by the fine metal particle M (labeled secondary antibody) held on the sensing surface 122 by antigen-antibody reaction, to generate randomly polarized scattered light L5 (refer to FIG. 4A). As illustrated in FIG. 4B, noise light L6 is generated in a position where the measuring light L4 totally-reflected a plurality of times is incident on the sensing surface 122.

The scattered light L5 and the noise light L6 generated in the predetermined areas of the sensing surface 122 enter the analyzer 140 via the aperture 144. The analyzer 140 only transmits an s-polarized component while eliminating other polarized components.

In this case, the noise light L6 holds a p-polarized state, and is eliminated by the analyzer 140 because of its crossed nicol relation with the analyzer 140. On the other hand, only the s-polarized component of the randomly polarized scattered light L5 is transmitted through the analyzer 140. The s-polarized component of the transmitted scattered light L5 is detected by the detection means 142, thereby enabling detection of the antigen R held in the predetermined area of the sensing surface 122 and determination of the amount thereof.

The aperture 144, the analyzer 140, and the detection means 142 are integrally moved from the end of the entrance side of the measuring light L4 to the end of the exit side to scan the sensing surface 122, thereby enabling detection of the s-polarized state of the scattered light L5 in all the areas of the sensing surface 122. Thus, the antigen R can be detected and the amount thereof can be determined in all the areas of the sensing surface 122.

In the sensing apparatus 110 of the embodiment, as in the case of the sensing apparatus 10, the scattered light L5 is detected via the analyzer 140 disposed in the crossed nicol relation to the polarizing direction of the measuring light L4. Thus, those other than the s-polarized component are eliminated from the transmitted light of the analyzer 140, in other words, the noise light L6 having a p-polarized state can be eliminated.

In the sensing apparatus 110, the noise light is eliminated by the analyzer 140 to enable selective detection of only the evanescent light scattered by the fine metal particles M. Thus, an S/N ratio can be increased, and highly accurate measurement can be carried out.

The noise light caused by the surface irregularities and the like of the sensing surface 122 can be eliminated. Thus, the surface of the slide glass does not need to be formed highly accurately. Even when an inexpensive slide glass low in forming accuracy is used, an S/N ratio can be increased, and highly accurate measurement can be carried out.

By allowing the measuring light L4 to totally be reflected on the sensing surface 122 a plurality of times, noise light may be generated from each total reflection position, increasing the amount of the noise light. However, in the case of the sensing apparatus 110 of the present invention, since the noise light can suitably be eliminated, even when the amount of the noise light increases, highly accurate measurement can be carried out without being affected by the increased amount.

In the sensing apparatus of this embodiment in which the aperture 144, the analyzer 140, and the detection means 142 are integrally moved to scan the sensing surface 122, primary antibodies each specifically bound to different antigens may be disposed for each predetermined interval or width of the sensing surface 122 in a scanning direction to capture varied antigens for each predetermined width. In other words, a plurality of types of antigens different from each other may be held for each predetermined width in its scanning direction on the sensing surface 122. Thus, by integrally moving the aperture 144, the analyzer 140, and the detection means 142 to scan the sensing surface 122, a plurality of types of antigens can be detected.

In the sensing apparatus 110 of the embodiment, as in the case of the sensing apparatus 10, the polarizer and the analyzer may include adjustment mechanisms for adjusting angles and positions so that the angles and the positions can be adjusted.

According to this embodiment, the p-polarized light is incident on the sensing surface 122. Not limited to this, however, s-polarized light may be incident on the sensing surface 122. In this case, the analyzer 140 is disposed to transmit only the p-polarized light with respect to the sensing surface 122.

This embodiment is not limited to the incidence of the p-polarized or s-polarized light on the sensing surface. Linearly polarized measuring light having a polarized surface inclined with respect to the sensing surface may be incident thereon. In the case of this embodiment, a wavelength plate for converting a polarized state of elliptically polarized noise light into a linearly polarized state may be disposed between the slide glass 120 and the analyzer 140, and the analyzer 140 only needs to be disposed in a crossed nicol relation to the light transmitted through the wavelength plate to be converted into the linearly polarized light.

As in the case of the sensing apparatus 10, this embodiment is not limited to the apparatus which holds the antigen R labeled by the labeled secondary antibody on the sensing surface by using the primary antibody (surface modification substance A1) and the secondary antibody (surface modification substance A2) specifically binding to the antigen (target substance R) through antigen-antibody reaction, and detects the antigen held on the sensing surface and determines the amount thereof.

The sensing apparatus of the present invention for detecting the scattered light of the evanescent light has been described in detail. A configuration similar to that of the sensing apparatus of the present invention can be applied to an apparatus for detecting scattered light of a surface plasmon (surface plasmon sensor). For example, the surface plasmon sensor includes a metal film on a dielectric prism, allows measuring light to be incident on an interface between the dielectric prism and the metal film under a condition of exciting a surface plasmon (entrance angle which becomes a surface plasmon resonance angle) to generate a surface plasmon on a surface of the metal film opposite the dielectric prism, and detects scattered light generated by scattering of the surface plasmon by fine metal particles which are scattering labels by detection means via an analyzer disposed so as to face the metal film and so as to be set in a crossed nicol relation to a polarizing direction of the measuring light. Even in this case, as in the case of the sensing apparatus illustrated in FIGS. 1A and 1B and 3, an S/N ratio can be increased, and highly accurate measurement can be carried out.

The sensing apparatus of the present invention has been described in detail. Needless to say, however, the present invention is not limited to the embodiments described above. Various improvements and changes can be made without departing from the gist and scope of the present invention.

EXAMPLES

Example 1

A specific antigen contained in blood plasma was detected by using the sensing apparatus 110 illustrated in FIG. 3.

MAS slide (by Matsunami Glass Ind., Ltd.) was used for a slide glass. A primary antibody was immobilized on a sensing surface of the MAS slide, and an antigen labeled by a labeled secondary antibody was bound to the primary antibody by a sandwich method to immobilize it to the sensing surface.

An SHG laser of a wavelength of 532 nm was used for a light source, and LAS-1000 (cooling CCD) for detection means.

A p-polarized measuring light was allowed to be incident on the sensing surface of the MAS slide to detect an antigen R. Results are indicated by a solid line in a graph of Example 1 of FIG. 5. In the graph of FIG. 5, an abscissa indicates, in a direction from an end of an entrance side of the MAS slide to an end of an exit side, positions (mm) when the end of the entrance side is a reference. An ordinate indicates the amount of light in each position. The amount of light is an integrated value of 10 pixels in an image shot by the LAS-1000 (cooling CCD).

Comparative Example 1

As Comparative Example 1, the detection of an antigen R was carried out under the same conditions as those of Example 1 except for removal of an analyzer from the sensing apparatus. Results are indicated by a broken line in a graph of Comparative Example 1 of FIG. 5.

Comparative Example 2

As Comparative Example 2, the detection of an antigen R was carried out under the same conditions as those of Example 1 except that an analyzer was disposed so that p-polarized light component is transmitted therethrough with respect to a sensing surface, in other words, in a state of being rotated by 90° as compared with Example 1. Results are indicated by a dashed line in a graph of Comparative Example 2 of FIG. 5.

Example 2

As Example 2, the detection of an antigen R was carried out under the same conditions as those of Example 1 except that s-polarized measuring light was allowed to be incident on a sensing surface of MAS slide, and an analyzer was disposed in a crossed nicol relation to the scattered light so that light having p-polarized light component is transmitted therethrough with respect to the sensing surface, in other words, scattered light (noise light) holding a polarized state of the s-polarized measuring light is eliminated. Results are indicated by a solid line in a graph of Example 2 of FIG. 6.

Comparative Example 3

As Comparative Example 3, the detection of an antigen R was carried out under the same conditions as those of Example 2 except for removal of an analyzer from the sensing apparatus. Results are indicated by a broken line in a graph of Comparative Example 3 of FIG. 6.

Comparative Example 4

As Comparative Example 4, the detection of an antigen R was carried out under the same conditions as those of Example 2 except that an analyzer was disposed so that s-polarized light component is transmitted therethrough with respect to a sensing surface, in other words, in a state of being rotated by 90° as compared with Example 2. Results are indicated by a dashed line in a graph of Comparative Example 4 of FIG. 6.

Comparative Example 5

Figure 7:
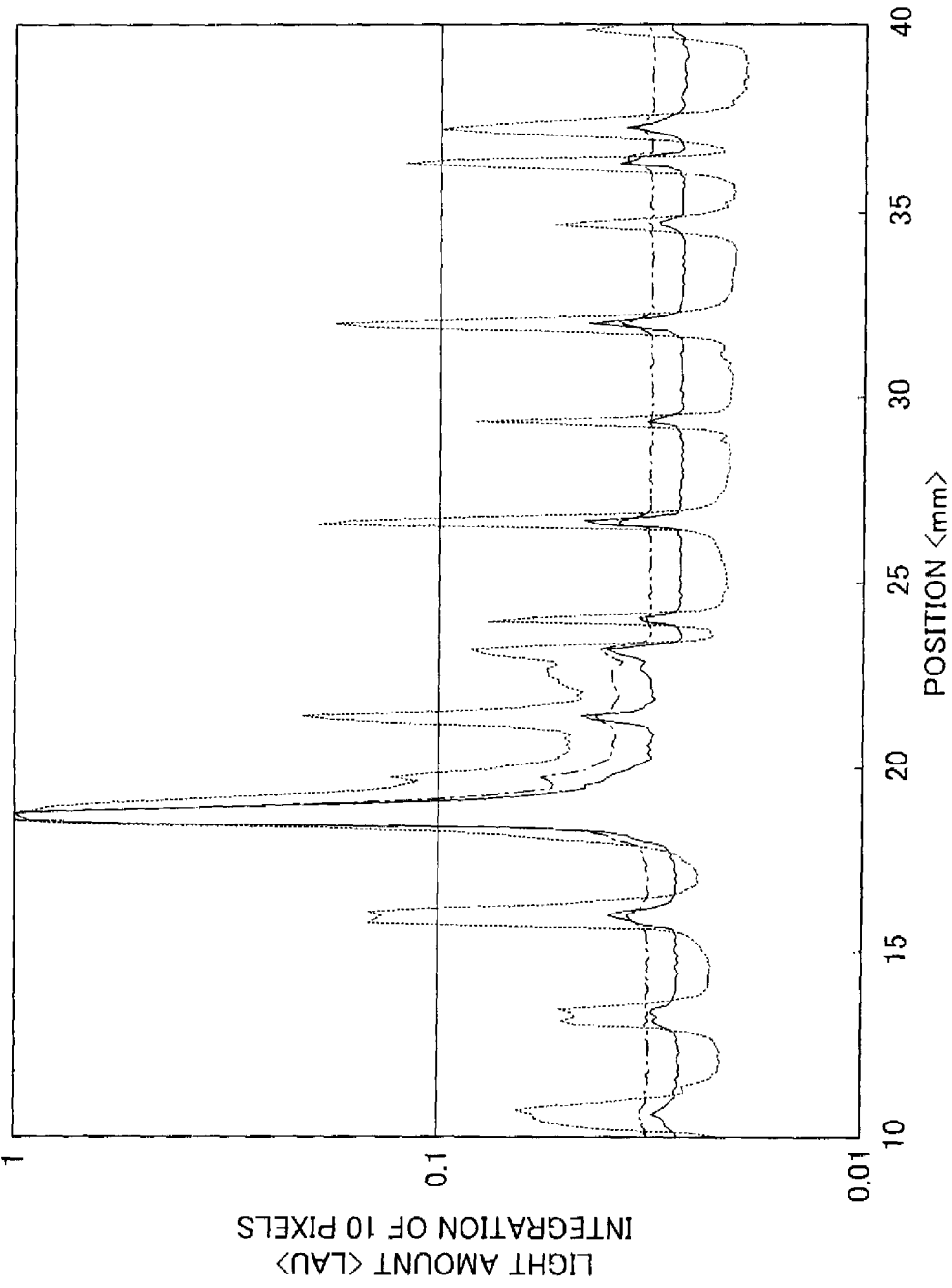
FIG. 7 is a graph illustrating normalized values of light amounts in Examples 1 and 2 and Comparative Example 5.

As Comparative Example 5, an average value was taken among light amount values in the measuring positions of Comparative Examples 1 and 3, which are measuring results when there is no analyzer, and was normalized by a maximum light amount value. Results are indicated by a broken line in a graph of Comparative Example 5 of FIG. 7. In the graph of FIG. 7, results of normalization similarly carried out in Examples 1 and 2 are respectively indicated by solid and dashed lines.

Figure 6:
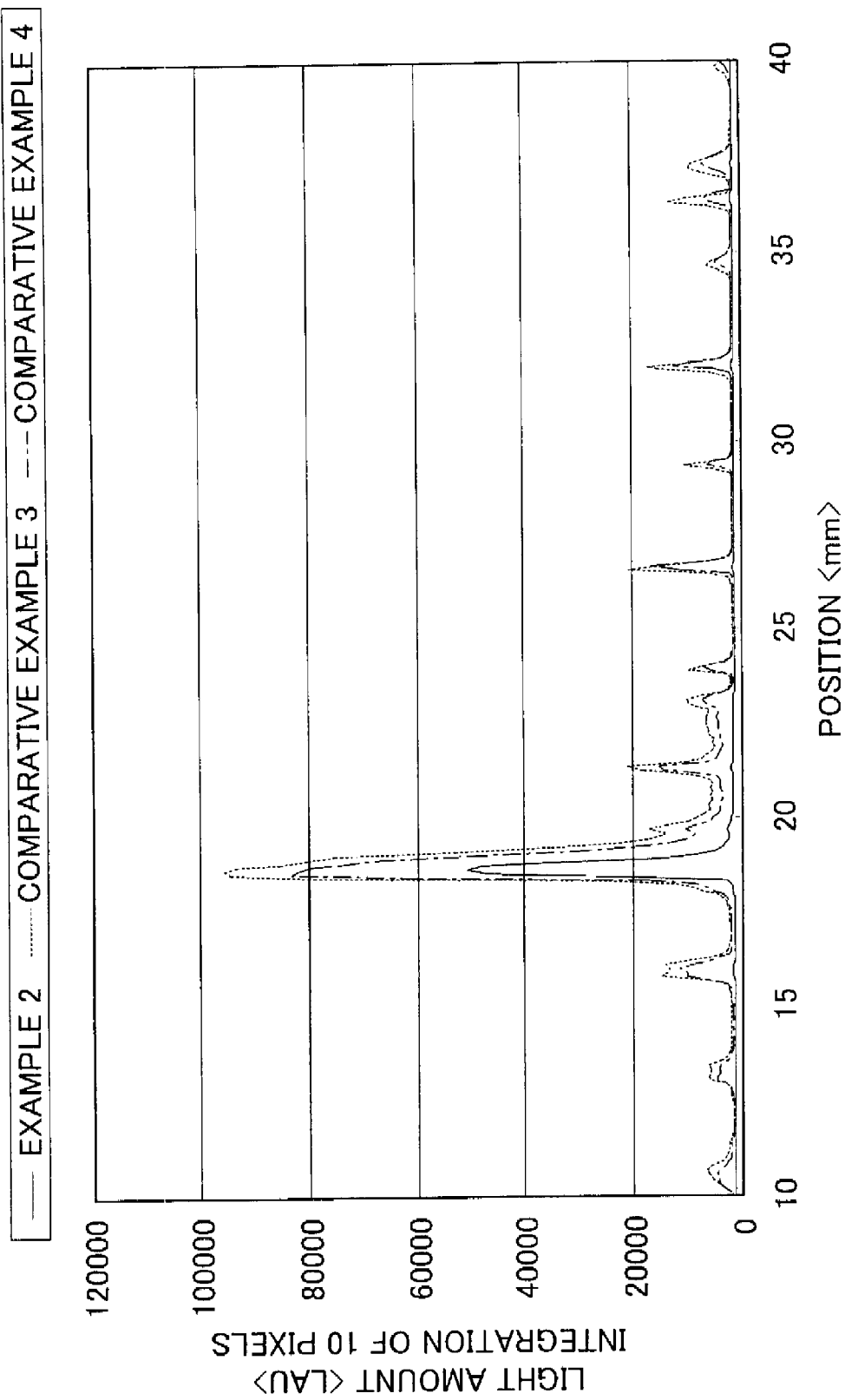
FIG. 6 is a graph illustrating measured values of light amounts in Example 2 and Comparative Examples 3 and 4.

As illustrated in FIGS. 5 and 6, in all the cases of Examples 1 and 2 and Comparative Examples 1 to 4, peaks are detected near 19 mm. This peak is caused by randomly polarized scattering light generated due to scattering of evanescent light by fine metal particles M, and is referred to as a main peak hereinafter.

In Comparative Examples 1 to 4, a plurality of peaks are detected in addition to the main peak.

As illustrated in FIG. 5, in Comparative Example 1 where the p-polarized measuring light is measured without using the analyzer and Comparative Example 2 where the analyzer is disposed so that p-polarized scattered light is transmitted therethrough with respect to the p-polarized measuring light, the amounts of light at peaks other than the main peaks are substantially the same.

Similarly, as illustrated in FIG. 6, in Comparative Example 3 where the s-polarized measuring light is measured without using the analyzer and Comparative Example 4 where the analyzer is disposed so that an s-polarized scattered light is transmitted therethrough with respect to the s-polarized measuring light, the amounts of light at peaks other than the main peaks are substantially the same.

On the other hand, as illustrated in FIGS. 5 to 7, in Examples 1 and 2 where the measuring light is measured by disposing the analyzer in the crossed nicol relation to the polarizing direction of the measuring light, the amounts of light at peaks other than the main peaks are extremely small as compared with Comparative Examples. Thus, the peaks other than the main peaks all exhibit scattered light holding polarized state of the measuring light. These peaks are caused by scattered light of the measuring light generated due to surface irregularities of the sensing surface.

As illustrated in FIG. 7, in Examples 1 and 2, the amounts of scattered light generated from measuring light due to surface irregularities of the sensing surface are considerably reduced. In other words, in Examples 1 and 2, by disposing the analyzer in the crossed nicol relation, the scattered light caused by the peaks other than the main peaks can be eliminated, and an S/N ratio can be increased.

What is claimed is:

1. A sensing apparatus, comprising:
   measuring light emission means for emitting measuring light of a predetermined polarized state;
   a waveguide member including a sensing surface which is modified by a surface modification substance so that only a specific target substance can be bound thereto, in which the measuring light entering therein under a condition of total internal reflection on said sensing surface is totally reflected to generate evanescent light on said sensing surface;
   detection means disposed at a side of said waveguide member or outside said waveguide member with respect to said sensing surface to detect an amount of scattered light of the evanescent light; and
   an analyzer disposed between said waveguide member and said detection means so as to face said sensing surface, wherein:
   said target substance is labeled by a fine metal particle selectively bound to said target substance;
   said measuring light emission means, said waveguide member, and said analyzer are included in an optical waveguide system which sets a polarized state of scattered light from said sensing surface generated when said target substance labeled by said fine metal particle is absent on said sensing surface in a crossed nicol relation to said analyzer; and
   the amount of the evanescent light scattered by said fine metal particle labeling said target substance bound to said surface modification substance modifying said sensing surface is detected by said detection means.

2. The sensing apparatus according to claim 1, further comprising an adjustment mechanism for adjusting a position of said analyzer,
   wherein said adjustment mechanism adjusts the position of said analyzer so that intensity of the scattered light, which is detected by said detection means via said analyzer, from said sensing surface generated when said target substance labeled by said fine metal particle is absent on said sensing surface is minimum.

3. The sensing apparatus according to claim 1,
   wherein said measuring light emission means includes a light source for emitting light of an optionally polarized state, and a polarizer for setting the light of the optionally polarized state emitted from said light source as the measuring light of the predetermined polarized state.

4. The sensing apparatus according to claim 3, further comprising an adjustment mechanism for adjusting a position of said polarizer,
   wherein said adjustment mechanism adjusts the position of said polarizer so that intensity of the scattered light, which is detected by said detection means via said analyzer, from the sensing surface generated when said target substance labeled by said fine metal particle is absent on said sensing surface is minimum.

5. The sensing apparatus according to claim 1, wherein said waveguide member includes a dielectric prism.

6. The sensing apparatus according to claim 1,
   wherein said waveguide member includes:
   a plate-shaped waveguide unit for totally reflecting the measuring light at least twice therein;
   an entrance unit disposed at one end of said plate-shaped waveguide unit to allow the measuring light to enter into plate-shaped waveguide member; and an exit unit disposed at another end of said plate-shaped waveguide unit to allow the measuring light totally reflected at least twice to travel to the outside of said waveguide member.

7. The sensing apparatus according to claim 1, wherein said measuring light emission means emits linearly polarized measuring light as the measuring light of the predetermined polarized state.

8. The sensing apparatus according to claim 1, wherein the measuring light emission means emits one of p-polarized measuring light and s-polarized measuring light as the measuring light of the predetermined polarized state to said sensing surface.

9. The sensing apparatus according to claim 1, wherein
said target substance is an antigen;
said surface modification substance is a primary antibody bindable to said antigen;
said fine metal particle contains secondary antibodies bindable to said antigen on the surface of said fine metal particle; and
the evanescent light scattered by said fine metal particle labeling said antigen held on said sensing surface by antigen-antibody reaction is detected by said detection means.

10. The sensing apparatus of claim 1, wherein the light emission means, the waveguide member and the analyzer are positioned in the cross nicol relation, independent of a wavelength of fluorescence of the target substance bound with the fine metal particles on the sensing surface, to improve SNR of the evanescent light at the detection means.

* * * * *